(12) United States Patent  
Berns et al.

(10) Patent No.: US 7,912,656 B2  
(45) Date of Patent: Mar. 22, 2011

(54) SYSTEM AND METHOD FOR PROVIDING AMPLITUDE SPECTROSCOPY OF A MULTILEVEL QUANTUM SYSTEM

(75) Inventors: David M. Berns, Boston, MA (US); Mark S. Rudner, Somerville, MA (US); Sergio O. Valenzuela, Sant Cugat (ES); William D. Oliver, Belmont, MA (US); Leonid S. Levitov, Brookline, MA (US); Terry P. Orlando, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 54 days.

(21) Appl. No.: 12/553,391

(22) Filed: Sep. 3, 2009

(65) Prior Publication Data

US 2010/0109638 A1    May 6, 2010

Related U.S. Application Data

(60) Provisional application No. 61/093,907, filed on Sep. 3, 2008.

(51) Int. Cl.
*G01N 21/00* (2006.01)
*G01N 22/00* (2006.01)

(52) U.S. Cl. .................................................... 702/28

(58) Field of Classification Search ............... 702/28
See application file for complete search history.

(56) References Cited

U.S. PATENT DOCUMENTS 6,584,413 B1* 6/2003 Keenan et al. .................. 702/28
6,635,106 B2* 10/2003 Katou et al. ..................... 96/67
6,898,533 B1* 5/2005 Miller et al. .................. 702/27

OTHER PUBLICATIONS

D.M. Berns et al., Amplitude spectroscopy of a solid-state artificial atom, Sep. 4, 2008, Nature, vol. 455, pp. 51-58, plus 16 pages of supplementary information.*
D.M. Berns et al., Amplitude spectroscopy of a solid-state artificial atom, May 11, 2008, arXiv:0805.1552 (Cornell Univeristy e-print service), 12 pages.*
M.S. Rudner et al., Quantum phase tomography of a strongly driven qubit, Nov. 7, 2008, Physical Review Letters, Nov. 7, 2008, vol. 101, 190502, 4 pages.*
M.S. Rudner et al., Quantum phase tomography of a strongly driven qubit, May 12, 2009, arXiv:0805.1555 (Cornell Univeristy e-print service), 5 pages.*

(Continued)

*Primary Examiner* — Evan Pert  
(74) *Attorney, Agent, or Firm* — Peter A. Nieves; Sheehan Phinney Bass + Green PA

(57) ABSTRACT

A system and method for providing amplitude spectroscopy is provided. Generally, the system contains a generator for providing a waveform for analysis of a multilevel quantum system, wherein the generator has the capability of changing amplitude of the waveform provided and driving the multilevel quantum system at a fixed frequency while sweeping amplitude. A detector is also provided for reading population in different energy states of the multilevel quantum system, wherein the detector plots an amplitude spectroscopy response of the multilevel quantum system. A memory and processor are provided within the system where the processor is configured by the memory to perform the step of plotting an energy-level diagram of the multilevel quantum system from the amplitude spectroscopy plot of the multilevel quantum system.

21 Claims, 10 Drawing Sheets

OTHER PUBLICATIONS

W.D. Oliver et al., Large-amplitude driving of a superconducting aftifical atom; Interferometry, cooling, and amplitude spectroscopy, Mar. 12, 2009, Quantum Information Processing, vol. 8, pp. 261-281.*

W.D. Oliver et al., Large-amplitude driving of a superconducting artificial atom; Interferometry, cooling, and amplitude sepectroscopy, May 31, 2009, arXiv:0906.0185 (Cornell University e-print service), 13 pages.*

S.O. Valenzuela et al., Microwave-induced cooling of a superconducting qubit, Dec. 8, 2006, Science, vol. 314, pp. 1589-1592.*

S.O. Valenzuela et al., Microwave-induced cooling of a superconducting qubit, Feb. 8, 2007, arXiv:cond-mat/0702190 (Cornell University e-print service), 19 pages.*

W.D. Oliver, Zehnder Interferometry in a Strongly Driven Superconducting Qubit, Dec. 9, 2005, Science, vol. 310, pp. 1653-1657.*

W.D. Oliver, Zehnder Interferometry in a Strongly Driven Superconducting Qubit, Dec. 29, 2005, arXiv:cond-mat/00512691 (Cornell University e-print service), 20 pages.*

* cited by examiner

SYSTEM AND METHOD FOR PROVIDING AMPLITUDE SPECTROSCOPY OF A MULTILEVEL QUANTUM SYSTEM

CROSS-REFERENCE TO RELATED APPLICATION

This application claims priority to U.S. Provisional Application entitled, "AMPLITUDE SPECTROSCOPY OF A SOLID-STATE ARTIFICIAL ATOM," having patent application Ser. No. 61/093,907, filed Sep. 3, 2008, which is entirely incorporated herein by reference.

GOVERNMENT SUPPORT

This invention was made with government support under Grant Number FA8721-05-C-0002 awarded by the Air Force, grant number F49620-01-1-0457 awarded by the Air Force Office for Sponsored Research, and grant number HR0011-06-C-0051 awarded by the Defense Advanced Research Projects Agency. The government has certain rights in this invention.

FIELD OF THE INVENTION

The present invention is generally related to spectroscopy, and more particularly is related to determining energy spectrums of multi-level quantum systems (including, but not limited to, natural and artificial atoms, molecules, defects, and impurities) by use of amplitude spectroscopy to sweep amplitude and then analyzing results of the amplitude sweeping.

BACKGROUND OF THE INVENTION

Since Newton's dispersion of light into a continuous color "spectrum," spectroscopy has been viewed primarily as a frequency-based technique. Bunsen, Foucault, Kirchhoff, and many others identified unique spectral lines for elements and compounds based on the emission and absorption of radiation at various frequencies. Spectroscopy has historically been used to obtain a wide range of information about nuclear, atomic, and molecular properties.

Early on, the determination of spectral lines, or energy levels, helped elucidate the principles of quantum mechanics through studies of the hydrogen atom and provided a means for testing atomic theory. Since then, several spectroscopy techniques to determine absolute transition frequencies (or, equivalently, wavelengths) have been developed, involving the emission, absorption, or scattering (e.g., Raman) of radiation. The series of spectral lines of hydrogen are named for Balmer and Rydberg, who observed them within and beyond the visible wavelengths. As previously mentioned, such frequency-dependent absorption and emission spectroscopy played a fundamental role in the development of quantum mechanics and the "new" atomic theory by identifying discrete energy levels.

With the invention of coherent high-intensity radiation sources at microwave (maser) and optical (laser) frequencies, with tunable, narrow spectral line-widths, targeted absorption spectroscopy of atoms and molecules with high frequency resolution is provided. The advent of tunable, coherent radiation sources at microwave and optical frequencies led to the age of modern atomic spectroscopy, where a primary approach is to identify absorption spectra of natural and artificial atoms and molecules as the source frequency v is varied to fulfill the resonance conditions $\Delta E = h\nu$, where $\Delta E$ is the energy-level separation and h is Planck's constant. The technique is now commonplace in research labs and usually involves shining a beam of light on a sample and watching how it absorbs light as the frequency of the radiation is swept through a range of values. An atom, for example, absorbs radiation at a specific set of frequencies that correspond to gaps between the energy levels of its electrons.

Spectroscopy has traditionally been viewed as a frequency-based measurement technique. Frequency-dependent absorption and emission spectroscopy has long played a fundamental role in the characterization of quantum systems. As previously mentioned, the development of coherent microwave (maser) and optical (laser) sources, high-intensity radiation with tunable, narrow spectral line-width, has further enabled targeted absorption spectroscopy of atoms and molecules with high frequency resolution. However, the application of broadband frequency spectroscopy is not universally straightforward. This is particularly relevant for certain classes of multi-level quantum systems (including, but not limited to, natural and artificial atoms, molecules, defects, impurities, which assume quantized energy levels that extend into microwave, millimeter wave and terahertz regimes. Although certainly not an impossible task, a broadband frequency-based spectroscopic study of such multilevel quantum systems in excess of around 50 GHz, becomes extremely challenging and expensive to implement due to numerous frequency-dependent effects (e.g., frequency dispersion and the requisite tolerances to control impedance), and due to the general requirement of multipliers that are inefficient and intrinsically noisy.

The abovementioned difficulty has been problematic for researchers performing studies on multilevel quantum systems, such as, for example, artificial atoms. Artificial atoms exhibit properties of ordinary atoms, including discrete energy levels. Such atoms could potentially be used to store and process data. Unfortunately, the problem in using artificial atoms as putative quantum-information systems is that the gaps between the levels tend to be in the problematic millimeter and microwave region.

Thus, a heretofore unaddressed need exists in the industry to address the aforementioned deficiencies and inadequacies.

SUMMARY OF THE INVENTION

Embodiments of the present invention provide a system and method for providing amplitude spectroscopy of a multilevel quantum system. Briefly described, in architecture, one embodiment of the system, among others, can be implemented as follows. The system contains: a generator for providing a waveform for analysis of a multilevel quantum system, wherein the generator has the capability of changing amplitude of the waveform provided and driving the multilevel quantum system at a fixed frequency while sweeping amplitude; a detector for reading population in different energy states of the multilevel quantum system, wherein the detector plots an amplitude spectroscopy response of the multilevel quantum system; a memory; and a processor configured by the memory to perform the step of plotting an energy-level diagram of the multilevel quantum system from the amplitude spectroscopy plot of the multilevel quantum system.

The present invention can also be viewed as providing methods for providing for providing amplitude spectroscopy of a multilevel quantum system. In this regard, one embodiment of such a method, among others, can be broadly summarized by the following steps: driving the multilevel quantum system at a fixed frequency, while sweeping amplitude;

determining an amplitude spectroscopy response of the multilevel quantum system driven toward saturation, where the amplitude spectroscopy response reflects a fixed frequency and a sweeping amplitude; and analyzing the amplitude spectroscopy response of the multilevel quantum system to derive an energy level structure of the multilevel quantum system.

Other systems, methods, and features of the present invention will be or become apparent to one with skill in the art upon examination of the following drawings and detailed description. It is intended that all such additional systems, methods, and features be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present system and method provides for use of amplitude spectroscopy. Amplitude spectroscopy is a technique that allows broadband spectroscopic characterization of a multilevel quantum system. With amplitude spectroscopy, spectroscopic information is obtained from the system response to driving field amplitude at a fixed frequency. The resulting spectroscopic interference patterns, referred to herein as "spectroscopy diamonds," or "diamonds", are mediated by multilevel Landau-Zener-Stückelberg (LZS) transitions and Mach-Zehnder-type interferometry, and they serve as a fingerprint of the multilevel energy spectrum of an atom. The energy spectrum is then determined by analyzing the atomic fingerprint. In this way, the amplitude spectroscopy technique complements frequency spectroscopy. Although a less direct approach, amplitude spectroscopy allows one to probe the energy level structure of a quantum system over extraordinarily large (even practically prohibitive) bandwidths by circumventing many of the challenges associated with a frequency-based approach.

It should be noted that although the present description refers to "artificial atoms" at times, the present system and method can be used in principle to identify the energy level structure (and any subsequent classification that this knowledge enables) of any atom, molecule, defect, or impurity with multiple energy levels that exhibit avoided crossings, either intrinsically or in the presence of a driving field, and whose quantum state can be driven by the application of a driving field towards, away, and/or through those level crossings. Specifically, although but one example of the broader applicability of amplitude spectroscopy, an artificial atom is used to demonstrate amplitude spectroscopy of a multilevel quantum system.

Figure 1:
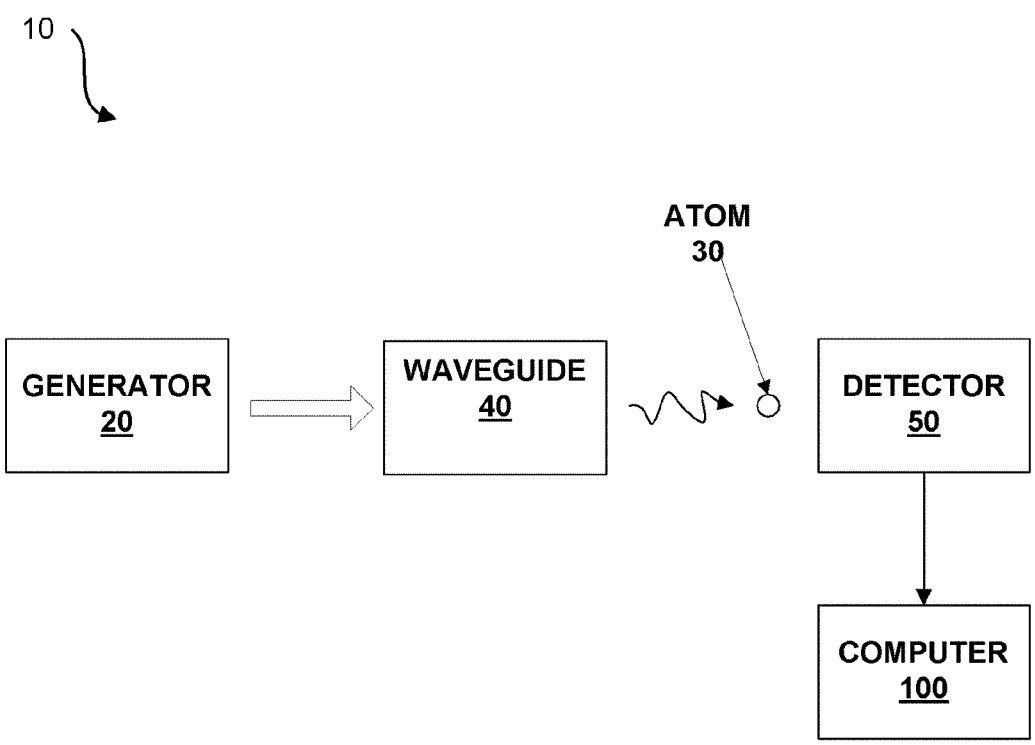
FIG. 1 is a schematic diagram illustrating an example of the present system for providing amplitude spectroscopy of an atom.

FIG. 1 is a schematic diagram illustrating an example of a system 10 that may be used to provide amplitude spectroscopy of an atom, in accordance with a first exemplary embodiment of the invention. As shown by FIG. 1, the system 10 contains a generator 20 for providing a waveform for analysis of an atom 30. For exemplary purposes, the atom is a superconducting quantum bit (qubit), such as a solid-state artificial atom that has discrete energy states that can be strongly coupled to external radio-frequency fields, which preserves quantum coherence. Artificial atoms are natural systems in which to probe a wide range of quantum effects, namely, coherent superpositions of macroscopic states, Rabi oscillations, microwave cooling, cavity quantum electrodynamics, and aspects of quantum measurement. As previously mentioned, the atom need not be an artificial atom, but may instead be any atom, molecule, defect, or impurity.

The generator 20 may be any known provider of a waveform, such as, but not limited to, a microwave generator or a laser. As is described in further detail herein, the generator 20 should have the capability of changing the amplitude of the waveform provided by the generator 20. The waveform provided by the generator 20 may be received by a waveguide 40 for focusing of the waveform onto the atom 30. Specifically, by use of the waveguide 40, for example, microwaves may be propagated down the waveguide 40 toward the atom 30. It should be noted that the use of a waveguide 40 is optional. As an example, if the generator 20 is a laser having a focused beam emitted therefrom, then there is no requirement for a waveguide 40.

A detector 50 is aligned with the atom 30 for reading the population in different energy states of the qubit 30. As an example, for a flux-qubit, the qubit state can be determined with a synchronous readout pulse applied to a superconducting quantum interference device (SQUID) magnetometer.

Figure 2:
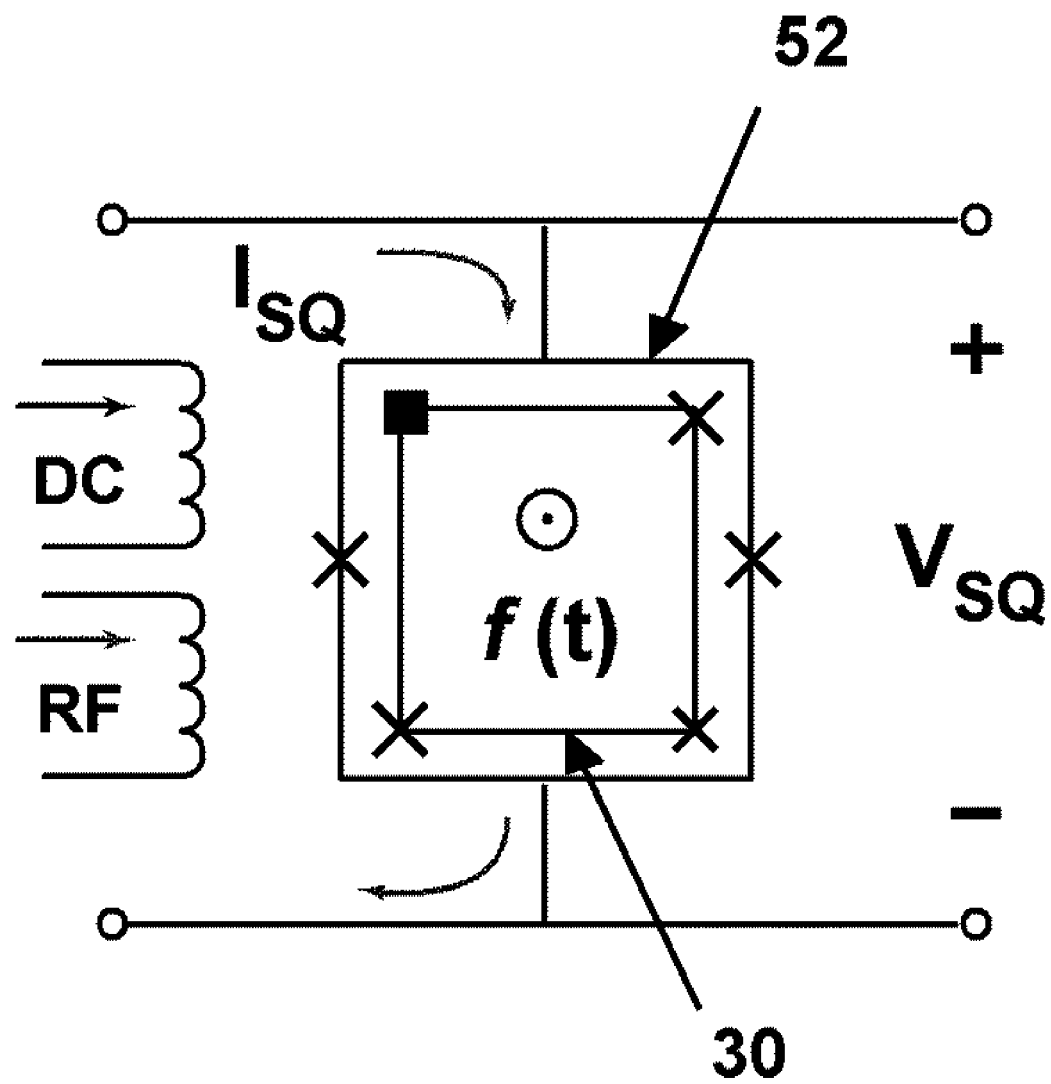
FIG. 2 further illustrates the detector of FIG. 1.

FIG. 2 further illustrates a detector 50, where the qubit 30 is surrounded by a SQUID magnetometer readout 52. Static (d.c.) and radio-frequency (RF) fields control the state of the qubit 30. As an example, a 3-µs cooling-pulse (11 MHz, 009 mV) followed by an amplitude spectroscopy pulse of duration $\Delta t$. The qubit state is read out using a SQUID current pulse, $I_{SQ}$, while monitoring the presence of a SQUID voltage $V_{SQ}$.

Readings from the detector are forwarded to a computer 100. In accordance with the present invention, the computer 100 is used to extract key features of the energy level structure of the atom so as to allow for reconstruction of the atom. An analysis of the amplitude spectroscopy response by the computer provides energy level slopes, the values of avoided crossings (energy splittings where two energy levels cross), and the positions of the avoided crossings. This information may then be used to identify the atom. Specifically, with this information the energy level diagram of the atom can be reconstructed and utilized.

Functionality for using the results of the detector 50 can be implemented in software, firmware, hardware, or a combination thereof. In a first exemplary embodiment, a portion of the present system 10 is implemented in software, as an executable program, and is executed by a special or general-purpose digital computer, such as a personal computer, workstation, minicomputer, or mainframe computer. The first exemplary embodiment of a general-purpose computer architecture that can implement the present system 10 is shown in FIG. 3.

Figure 3:
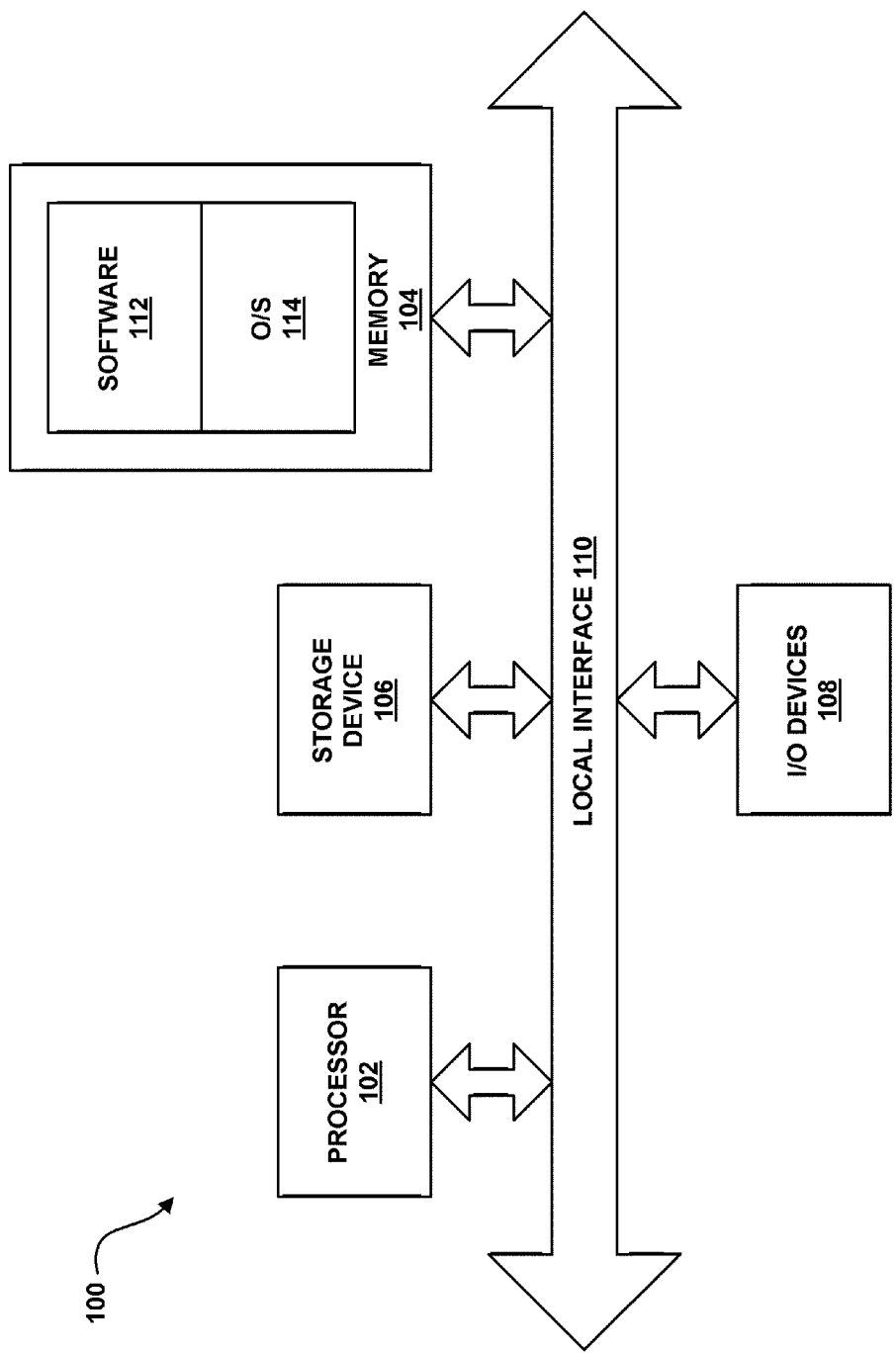
FIG. 3 further illustrates the computer/computational component of FIG. 1.

Generally, in terms of hardware architecture, as shown in FIG. 3, the computer 100 includes a processor 102, memory 104, storage device 106, and one or more input and/or output (I/O) devices 108 (or peripherals) that are communicatively coupled via a local interface 110. The local interface 110 can be, for example but not limited to, one or more buses or other wired or wireless connections, as is known in the art. The local interface 110 may have additional elements, which are omitted for simplicity, such as controllers, buffers (caches), drivers, repeaters, and receivers, to enable communications. Further, the local interface 110 may include address, control, and/or data connections to enable appropriate communications among the aforementioned components.

The processor 102 is a hardware device for executing software 112, particularly that stored in the memory 104. The processor 102 can be any custom made or commercially available processor, a central processing unit (CPU), an auxiliary processor among several processors associated with the computer 100, a semiconductor based microprocessor (in the form of a microchip or chip set), a macroprocessor, or generally any device for executing software instructions.

The memory 104 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 104 may incorporate electronic, magnetic, optical, and/or other types of storage media. Note that the memory 104 can have a distributed architecture, where various components are situated remote from one another, but can be accessed by the processor 102.

The software 112 in the memory 104 may include one or more separate programs, each of which comprises an ordered listing of executable instructions for implementing logical functions of the present system 10, as described below. In the example of FIG. 3, the software 112 in the memory 104 defines the system 10 functionality in accordance with the present invention. In addition, the memory 104 may contain an operating system (O/S) 114. The operating system 114 essentially controls the execution of computer programs and provides scheduling, input-output control, file and data management, memory management, and communication control and related services.

The system 10 may be provided by a source program, executable program (object code), script, or any other entity containing a set of instructions to be performed. When a source program, then the program needs to be translated via a compiler, assembler, interpreter, or the like, which may or may not be included within the memory 104, so as to operate properly in connection with the O/S 114. Furthermore, the system 10 can be written as (a) an object oriented programming language, which has classes of data and methods, or (b) a procedure programming language, which has routines, subroutines, and/or functions.

The I/O devices 108 may include input devices, for example but not limited to, a keyboard, mouse, scanner, microphone, etc. Furthermore, the I/O devices 108 may also include output devices, for example but not limited to, a printer, display, etc. Finally, the I/O devices 108 may further include devices that communicate via both inputs and outputs, for instance but not limited to, a modulator/demodulator (modem: for accessing another device, system, or network), a radio frequency (RF) or other transceiver, a telephonic interface, a bridge, a router, etc.

When the system 10 is in operation, the processor 102 is configured to execute the software 112 stored within the memory 104, to communicate data to and from the memory 104, and to generally control operations of the computer 100 pursuant to the software 112. The software 112 and the O/S 114, in whole or in part, but typically the latter, are read by the processor 102, perhaps buffered within the processor 102, and then executed.

When the system 10 is implemented in software, as is shown in FIG. 3, it should be noted that the system 10 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The system 10 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the system 10 is implemented in hardware, the system 10 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Having generally described the devices in the present system and method, the following further describes the processes used in the present system and method for providing amplitude spectroscopy of an atom.

Figure 4:
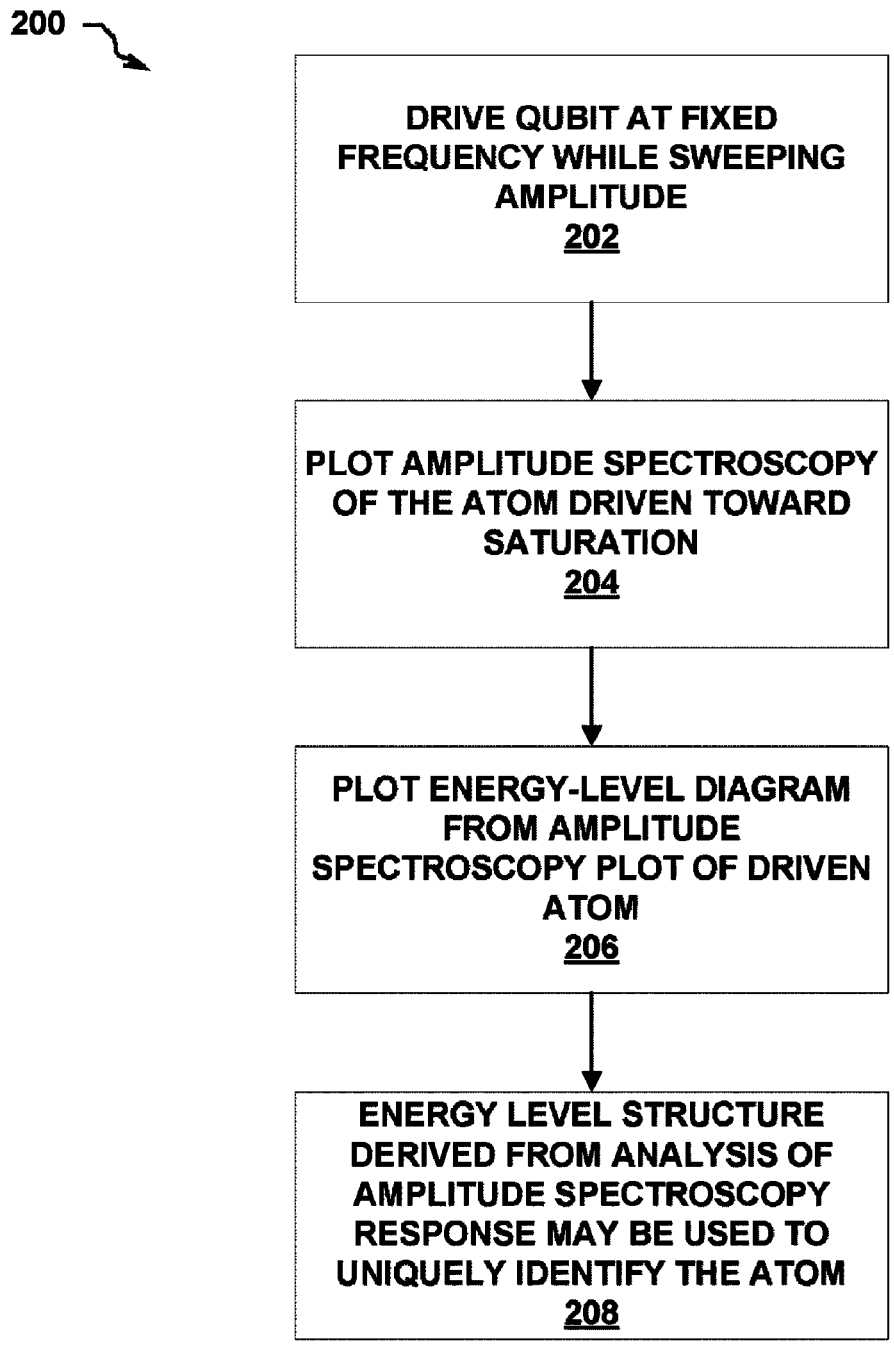
FIG. 4 is a flowchart illustrating a general method for providing amplitude spectroscopy of an atom.

FIG. 4 is a flowchart 200 illustrating a general method for providing amplitude spectroscopy of an atom. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. In the description of the exemplary demonstration "atom", "artificial atom", and "qubit" are used interchangeably.

As is shown by block 202, the qubit 30 is driven at a fixed frequency v, while a driving amplitude V is swept for each static flux detuning $\delta f_{dc}$. Specifically, the qubit 30 is driven longitudinally with a time-dependent flux represented by equation 1 (Eq. 1).

$$\delta f(t) = \delta f_{dc} - \Phi_{rf} \sin \omega t \quad \text{(Eq. 1)}$$

The time-dependent flux induces sinusoidal excursions through the energy levels about a static flux bias $\delta f_{dc}$, where the driving amplitude $\Phi_{rf} = \alpha V$ is proportional to the source voltage V with a frequency-dependent constant of proportionality α.

To reach a regime dominated by Landau-Zener transitions at level crossings, which is necessary to determine locations of energy levels, the driving frequency, represented as $v = \omega/2\pi$, is chosen such that hv is generally much smaller that the instantaneous energy-level spacing throughout the driving cycle, but the evolution through level crossings is non-adiabatic.

The transition rate between the states q and q' is controlled by the relative-energy sweep rate represented by equation 2 (Eq. 2).

$$\zeta_i = h(|m_q| + |m_{q'}|)\frac{d}{dt}\delta f \bigg|_{t=t_i} \quad \text{(Eq. 2)}$$
$$= h(|m_q| + |m_{q'}|)\Phi_{rf}\omega\cos\omega t_i$$

The relative-energy sweep rate is evaluated at the time $t_i$ at which the atom is swept through an avoided crossing $\Delta_{q,q'}$. Here $m_q = h^{-1} dE_q/df$ is the diabatic energy-level slope of state q in units of frequency per flux. In this regime, a Landau-Zener transition at an avoided crossing with energy splitting $\Delta_{q,q'}$ occurs with probability illustrated by equation 3 (Eq. 3)

$$P_{LZ} = 1 - \exp\left(-\frac{\pi\Delta_{q,q'}^2}{2\hbar\zeta_i}\right) \quad \text{(Eq. 3)}$$

In equation 3, $\hbar = h/2\Pi$. Such transitions drive the system into a coherent superposition of energy eigenstates associated with different wells.

Repeated Landau-Zener transitions give rise to Stückelberg oscillations in the populations of the states q and q'. For a crossing $\Delta_{q,q'}$, and using a fixed driving frequency v, the resulting interference patterns depend on the driving amplitude $\Phi_{rf}$ through the sweep rate $\zeta_i$ and on the static flux bias $\delta f_{dc}$ through the times $t_i$. Analyzing the interference patterns in ($\Phi_{rf}$, $\delta f_{dc}$) space, therefore, allows us to obtain spectroscopic information about the atom. Since the rate $\zeta_i$ is proportional to both amplitude and frequency, one can accommodate a small driving frequency by compensating with a large driving amplitude at an appropriate static flux bias. This also allows one to control the time interval between consecutive Landau-Zener transitions through a given crossing. For Stükelberg interference to occur, this time interval, which is typically a small fraction of the driving period 1/v, must be smaller than relevant decoherence times.

Figure 5:
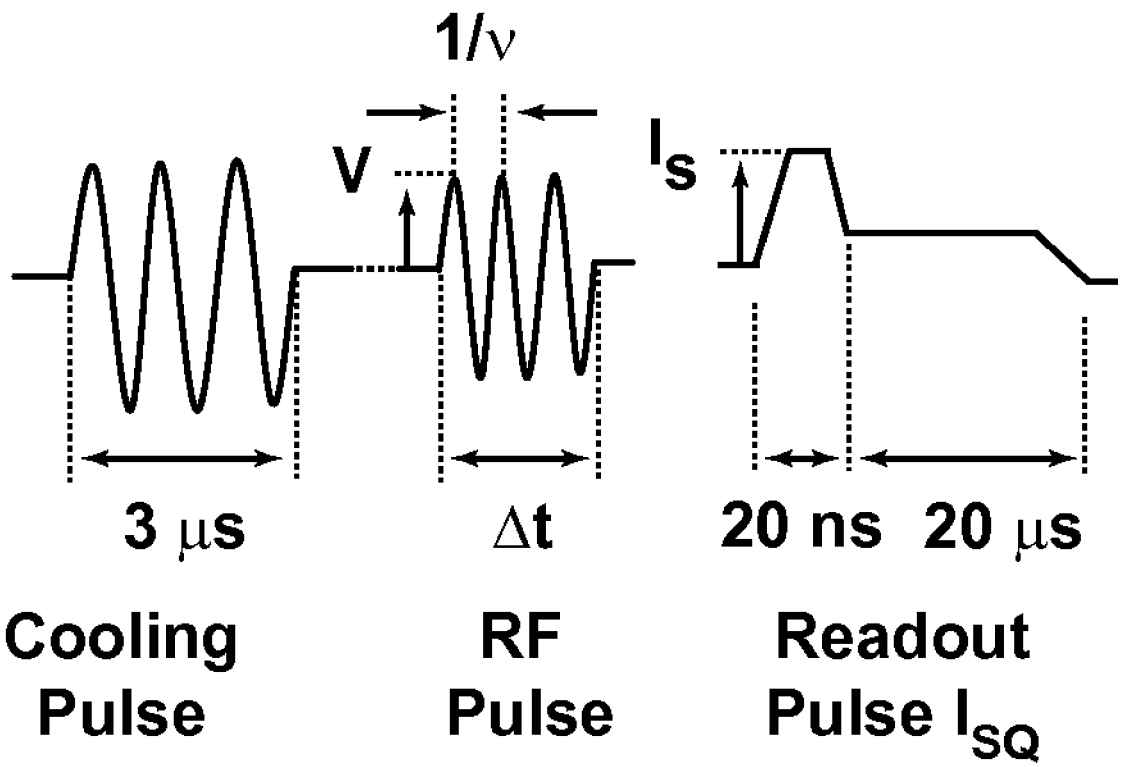
FIG. 5 is a schematic diagram of a pulse sequence used in accordance with the present system and method.

For exemplary purposes, the pulse sequence shown in FIG. 5 is used, which consists of a harmonic cooling pulse to initialize the qubit 30 in its ground state, followed by the desired amplitude spectroscopy pulse. The qubit state is determined by applying a synchronous readout pulse to the SQUID magnetometer. Using this technique, both the long-time and short-time behavior of the qubit 30 can be investigated in accordance with the present invention. In addition, one can determine the energy-level slopes $m_q$ along with the splittings $\Delta_{q,q'}$ and d.c.-flux locations $\delta f_{q,q'}$ of level crossings that constitute the energy-level diagram.

Figure 6:
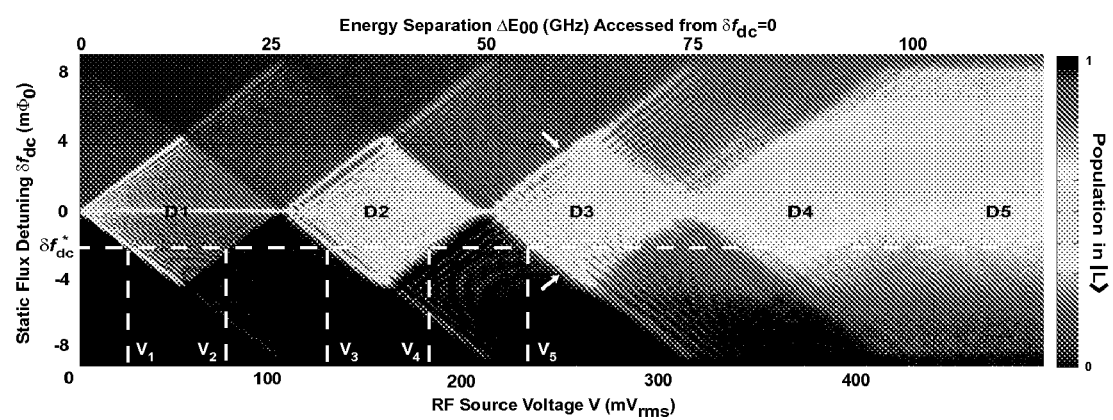
FIG. 6 is a schematic diagram illustrating the amplitude spectroscopy of the qubit of FIG. 1, driven toward saturation.

Returning to FIG. 4, the amplitude spectroscopy of the atom 30 driven toward saturation is plotted (block 204). FIG. 6 is a schematic diagram illustrating the amplitude spectroscopy of the atom 30 driven toward saturation. The resulting spectroscopy diamonds exhibit interference patterns and population inversion that serve as a fingerprint of the spectrum of the atom 30. Four primary spectroscopy diamond D1, D2; D3, D4 with large population contrast, centered about $\delta f_{dc} = 0$, are observed in the data, which are flanked by eight fainter diamonds. The diamond structures result from the interplay between static flux detuning and driving amplitude, which determine when the various level crossings are reached. Since the onset of each diamond is associated with transitions at a particular level crossing, the boundaries of the diamonds mark the occurrence of level crossings. The linear relation between V and $\Phi_{rf}$ are used to obtain values of $\delta f_{q,q'}$ listed in table 1 below. Specifically, table 1 provides an example of energy spectrum parameters determined using amplitude spectroscopy. It should be noted that the numerical values shown in table 1 are merely provided for exemplary purposes.

TABLE 1

| Crossing, q, q' | Location, $\delta f_{q, q'}$ (m$\Phi_0$) | Magnitude, $\Delta_{q, q'}/h$ (GHz) | Energy-level slope, $m_{q'}$ (GHz m$\Phi_0^{-1}$) |
|---|---|---|---|
| 0, 0 | 0 | 0.013 ± 0.001 | 1.44 ± 0.01 |
| 0, 1 | 8.4 ± 0.2 | 0.09 ± 0.005 | 1.09 ± 0.03 |
| 0, 2 | 17.0 ± 0.2 | 0.40 ± 0.01 | 0.75 ± 0.04 |
| 0, 3 | 25.8 ± 0.4 | 2.2 ± 0.1 | 0.49 ± 0.08 |

Returning to FIG. 4, an energy-level diagram (enlarged and not-to-scale for purposes of visualization) is plotted from the amplitude spectroscopy plot of the driven qubit (block 206). Plotting is performed by the computer 100. It should be noted that many different techniques may be used to derive the energy level diagram from the amplitude spectroscopy plot of the driven qubit. The following provides examples of techniques that may be used to derive the energy level diagram, however, it should be noted that the following merely provides examples that may be used and the invention is not intended to be limited to the techniques described herein.

Figure 7:
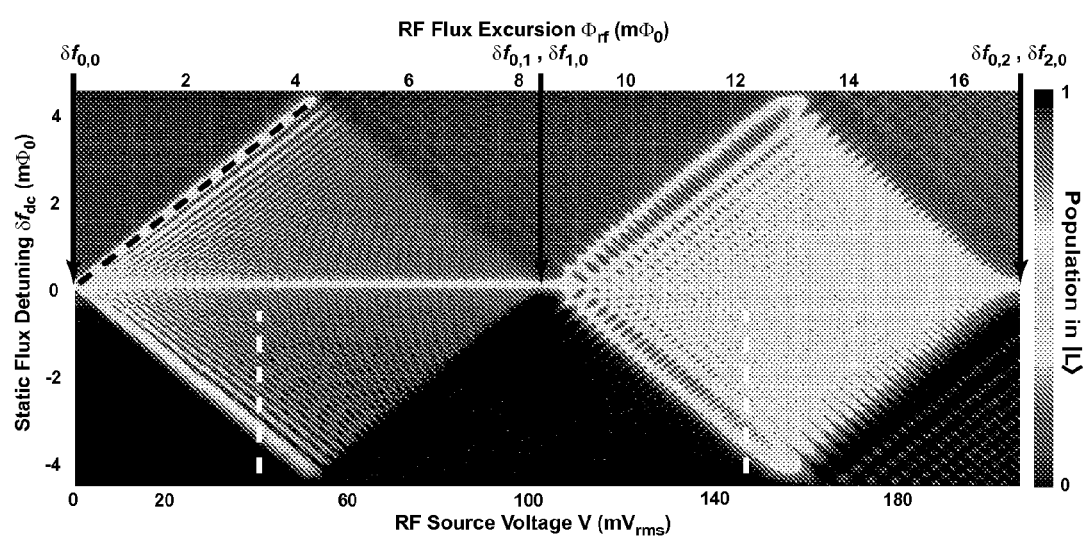
FIG. 7 is a plotting of the first diamond D1 and the second diamond D2 interference patterns due to a single (D1) and multiple (D2) avoided crossings.

For the particular static flux detuning $\delta f_{dc} = \delta f^*_{dc}$, as illustrated in FIG. 5 and FIG. 6 by dashed lines, the cooling pulse prepares the qubit 30 in the ground state, |0, L⟩. As the amplitude of the spectroscopy pulse is increased from V=0, population transfer from |0, L⟩ to |0, R⟩ first occurs at V=$V_1$, where the $\Delta_{0,0}$ crossing is reached (FIG. 6, left-hand side of D1; other level-crossing voltages are similarly labeled $V_2, \ldots, V_5$). For $V_1 < V < V_2$, Stüickelberg interference at the $\Delta_{0,0}$ crossing results in the observed fringe contrast of FIG. 7. FIG. 7 is a plotting of D1 and D2 interference patterns due to a single (D1) and multiple (D2) avoided crossings. It is noted that there is strong population inversion in D2 and that there is cooling in the region between D1 and D2 as well as at interference nodes in D2. Arrows indicate the locations $\delta f_{q,q'}$ of avoided crossings, as shown on the top axis.

Figure 8:
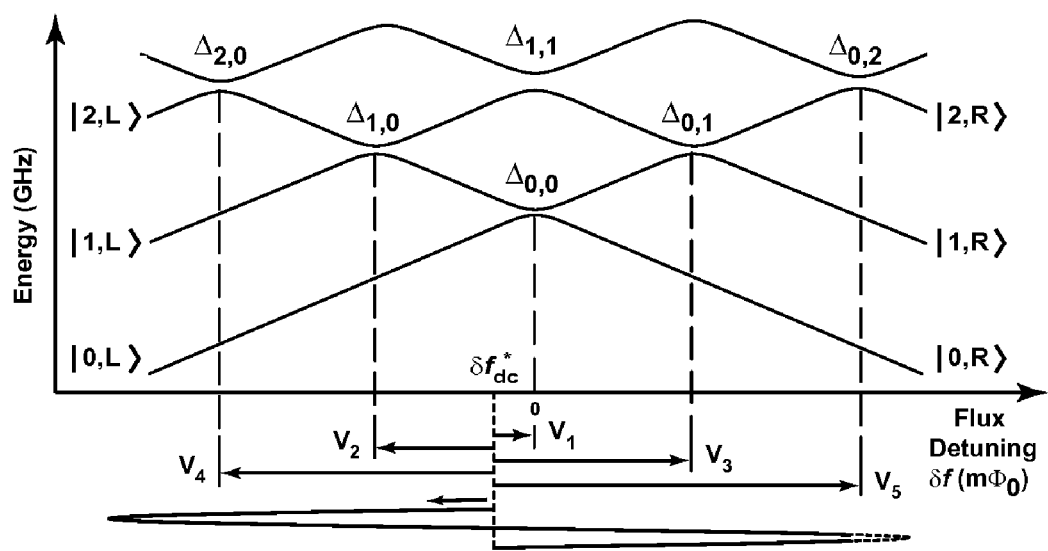
FIG. 8 is an energy level diagram illustrating the relation between the driving amplitude and the level-crossing positions for a particular static flux detuning.

FIG. 8 is an energy level diagram illustrating the relation between the driving amplitude V and the level-crossing positions for a particular static flux detuning $\delta f_{dc} = \delta f^*_{dc}$. Specifically, an analysis of the amplitude spectroscopy response provides information such as the energy level slopes, the values of avoided crossings, and the positions of the avoided crossings. With this information, one can reconstruct the energy level diagram of FIG. 8. Arrows in FIG. 8 represent the amplitudes $V_1$-$V_5$ at which the crossings are reached, marking the edges of the spectroscopic diamonds in FIG. 6.

Referring to both FIGS. 6 and 8, at $V=V_2$, the adjacent crossing, $\Delta_{1,0}$ is reached, inducing transitions between levels $|0, R\rangle$ and $|0, L\rangle$ and marking the right-hand side of D1. For $V_2 < V < V_3$, the data show a large reduction in contrast due to the addition of a single, strong transition at $\Delta_{1,0}$. The saturated population depends on the competition between transitions at $\Delta_{0,0}$ and $\Delta_{1,0}$, on relatively fast intra-well relaxation and to a lesser extent, on much slower inter-well relaxation processes. In the qubit 30, because $\Delta_{0,0} \ll \Delta_{1,0}$, the dominant transitions occur at the $\Delta_{1,0}$ crossing. Transitions $|0,L\rangle \to |0,R\rangle$ are still induced at the $\Delta_{0,0}$ crossing, but constructive Stückelberg interference at $\Delta_{1,0}$ converts a substantial fraction of that population to $|1, L\rangle$, an excited state of the left-hand well. Since relaxation within a well is a relatively fast process in this qubit in comparison with the relaxation between wells, the excited state population tends to relax back to the ground state, $|0, L\rangle$, thus suppressing the net population transfer. In contrast, for values of V such that the interference at $\Delta_{1,0}$ is destructive, the population remains in $|0, R\rangle$, making the interference fringes arising from $\Delta_{0,0}$ visible, albeit with reduced contrast (FIG. 6, faint diamond: FIG. 7). For $V_2 < V < V_3$, the qubit can be cooled to its ground state.

At even larger amplitudes, transitions to additional excited states become possible. For $V > V_3$, the qubit 30 can make transitions between $|0,L\rangle$ and $|1,R\rangle$, marking the left-hand side of D2. The right-hand side of D2 is marked by the amplitude, $V=V_4$, where $\Delta_{2,0}$ is reached, allowing transitions between $|0,R\rangle$ and $|2,R\rangle$. This description can be extended straightforwardly to the remainder of the spectrum, and therefore further explanation is not provided herein.

There are several notable features associated with amplitude spectroscopy, as provided by the present invention. First, the qubit 30 can be probed continuously over an extremely broad bandwidth. In particular, for exemplary purposes, spectroscopy diamond D5 (FIG. 6) results from transitions to energy levels more than $h \times 100$ GHz above the ground state. Even at such high energy levels, the qubit 30 retains its energy-level structure in the presence of the strong driving field used to probe it. Second, a single driving frequency can be used, for example, only 0.16 Generally, for double-well systems, the splittings $\Delta_{q,q'}$ tend to increase in higher excited states (FIG. 8). In such cases, the entire spectrum can be mapped using a single frequency, or a small range of frequencies, because the larger driving amplitudes required to reach those larger splittings $\Delta_{q,q'}$ also provide the larger sweep rates required to probe them.

Third, the second diamond D2 shows strong population inversion due to the competition between transitions to the respective excited states $|1,L\rangle$ and $|1,R\rangle$ at avoided crossings $\Delta_{1,0}$ and $\Delta_{0,1}$ combined with fast intrawell relaxation to $|0,L\rangle$ and $|0,R\rangle$ (FIG. 7). The transition rates at $\Delta_{1,0}$ and $\Delta_{0,1}$ have strong oscillatory behavior due to Stückelberg interference, which is constructive or destructive depending on the values of $\delta f_{dc}$ and V. The competition between these rates leads to the observed checkerboard pattern, symmetric about $\delta f_{dc}=0$, with alternating regions of strong population inversion and efficient cooling, depending on the specific well (left-hand well or right-hand well) in which the relaxation occurs. Similar checkerboard patterns are present in the diamonds D3 and D4. The population inversion observed here can be used as the active medium of a single-or multi-atom laser.

As previously mentioned, many different techniques may be used to derive the energy level diagram from the amplitude spectroscopy plot of the driven qubit. As an example, energy level slopes may be determined. Energy level slopes can be derived from fitting the diamond (Stückelberg interference) patterns from the response of the atom driven for long times (driven into saturation). Energy level slopes can also be derived from the 2D Fourier transform of the amplitude response, or from the diamond (Stückelberg interference) patterns from the response of the atom driven for short times.

Avoided crossing values may also be determined. As an example, avoided crossing values (splittings) can be derived from fitting the diamond (Stückelberg interference) patterns from the response of the atom driven for long times (driven into saturation). In addition, avoided crossing values (splittings) can be derived from fitting the diamond (Stückelberg interference) patterns from the response of the qubit driven for short times.

Positions of avoided crossing values may also be determined to assist in deriving the energy level diagram from the amplitude spectroscopy plot of the driven qubit. As an example, the vertices of the diamonds provide the flux positions of the avoided crossings. Equivalently, one can extrapolate the diamond edges back to the flux axis (vertical axis on diamond plots) in order to find their location in flux.

The following further describes certain of these techniques for deriving the energy level diagram from the amplitude spectroscopy plot of the driven qubit.

The energy-level separation $\Delta E_{q,q'} = h(|m_q| + |m_{q'}|)(\delta f_{dc} - \delta f_{q,q'})$ between states $|q,L\rangle$ and $|q',R\rangle$ s proportional both to the net flux detuning from the location $\delta f_{q,q'}$ of the avoided crossing $\Delta_{q,q'}$, and to the sum of the magnitudes of the energy-level slopes $m_q$ and $m_{q'}$. Since the relative phase accumulated between the $|q,L\rangle$ and $|q',R\rangle$ components of the wavefunction over repeated Landau-Zener transitions is sensitive to $\Delta E_{q,q'}$, the slopes can be derived from the interference patterns, which arise when $\delta f_{dc}$ is varied. The Nth node in the interference pattern, where a 'node' indicates a minimal change in the states' populations, occurs when a relative phase or $2\pi N$ is accumulated between transitions. For sinusoidal driving, the locations of the nodes (in $\delta f_{dc}$) follow the power law $s_{q,q'} N^{2/3}$, with a prefactor $s_{q,q'}$ related to the energy-level slopes by equation 4 below $$|m_q| + |m_{q'}| = bv\sqrt{\frac{\alpha V}{s_{qq'}^3}}, \quad \text{(Eq. 4)}$$

where $b=3\pi/2\sqrt{2}$ and $\alpha$ is the frequency-dependent conversion factor between radio-frequency flux and source voltage. For exemplary purposes, the value of this frequency-dependent conversion factor at $v=0.16$ GHz. $\alpha=0.082\, m\chi_0 mV_{rms}^{-1}$, is inferred from the slope of the left-hand edge of D1 (FIG. 7). The $N^{2/3}$ power-law fits to the nodes of the vertical slices in D1 and D2, which are used to extract $m_0$ and $m_1$ (FIG. 7, dashed vertical lines), where we take $|m_q|=|m_{q'}|\equiv m_q$ for $q=q'$ in the qubit 30. The slopes are obtained sequentially from the fitted values $s_{q,q'}$ in equation 4, starting with $2m_0=2.88$ GHz $m\Phi_0^{-1}$ followed by $m_0+m_1=2.534$ GHz $m\Phi_0^{-1}$. The values are summarized in table 1 above.

As an alternative way to analyze the data, as mentioned above, one can use the discrete two-dimensional Fourier transform (2DFT). To see the benefits of the 2DFT, it is noted that the amplitude spectroscopy plots in FIGS. 6 and 7 display structure on several scales. On the largest scale, the boundaries of the spectroscopy diamonds are readily identifiable, and on a smaller scale, the interiors of the diamonds are textured by fringes arising from the interference between successive Landau-Zener transitions at a single or multiple avoided crossings. On an even smaller scale, these fringes are composed of a series of horizontal multi-photon resonance lines. To extract information from these small-scale structures, it is helpful to apply a transformation that is able to invert length scales; the 2DFT does this.

In particular, the 2DFT allows for determining of the relation between the slopes $m_0$ and $m_1$ in a very clear and direct fashion. The observed structure in the first two diamonds arises from the underlying 'Bessel-function staircases' of multi-photon resonances associated with transitions between the four lowest energy levels, where the n-photon absorption rate depends on driving amplitude through the square of the Nth-order Bessel function.

The amplitude spectroscopy data typically exhibit complex checkerboard patterns of Stückelberg oscillations originating from several level crossings, superimposed with multi-photon resonance structure on a finer scale. Extracting spectroscopic information from these structures is facilitated by the 2DFT, which yields Fourier intensity localized near lemon-shaped oval curves in Fourier space. The following describes how these results can be used to extract the parameters of the qubit energy spectrum from the data. It should be noted that this is merely provided as an example.

We start with the first diamond (D1), in which qubit magnetization exhibits Stückelberg oscillations arising from interference of repeated passages through the level crossing $\Delta_{0,0}$. The main features of the 2DFT of the magnetization can be understood by studying the 2DFT of the transition rate at the qubit level crossing in this regime.

The 2DFT of the transition rate displays intensity concentrated along the two curves as shown by equation 5

$$k_{\tilde{V}} = \pm \frac{2}{v} \sin\left(\frac{v}{2} k_{\tilde{\delta f}_{dc}}\right), \quad \text{(Eq. 5)}$$

where the flux detuning and the driving signal are measured in the energy units as shown by equation 6.

$$\tilde{\delta f}_{dc} = 2|m_0|\delta f_{dc} \quad \text{(Eq. 6)}$$

In addition, $\tilde{V} = 2|m_0|\alpha V$. After going back to the physical units, Eq. 5 gives the following equation 7.

$$k_V = \pm \frac{4|m_0|\alpha}{v} \sin\left(\frac{v}{4|m_0|} k_{\delta f_{dc}}\right) \quad \text{(Eq. 7)}$$

The simplicity of the result can be traced to the fact that the curve of equation 5 reproduces time evolution of the quantum phase of the qubit, which is harmonic for harmonic driving.

Most strikingly, the apparently distinct phenomena of interference fringes and multi-photon resonances observed in the real space image are manifested as a single smooth curve in Fourier space. This structure can be understood by considering $k_V$ and $k_{\delta f_{dc}}$ to be smoothly varying functions of the spatial coordinates (V, $\delta f_{dc}$) and applying the stationary phase analysis to Fourier integrals.

The situation in the second diamond is somewhat more complicated. In numerical simulations it is noted that the steady-state magnetization in D2 was well reproduced by a simple rate model based on incoherently adding two additional transition rates to account for transitions at the avoided crossings with the left and right first-excited states. These additional rates are calculated using an appropriate value of energy level splitting $\Delta_{0,1}$ (approximately 90 MHz), and also take into account the different slopes of the ground and excited state energy levels. In this model, the lemon structure in the Fourier image of D2 is approximated as the sum of the Fourier transforms of the three relevant transition rates. Due to the difference in the dispersion of the lowest and second-lowest qubit energy levels versus dc flux bias, for the $\Delta_{01}$ and $\Delta_{10}$ level crossings we have equation 8 below.

$$\tilde{\delta f}_{dc} = (|m_0| + |m_1|)\delta f_{dc}, \tilde{V} = (|m_0| + |m_1|)\alpha V \quad \text{(Eq. 8)}$$

This provides a sinusoid as shown by equation 9.

$$k_V = \pm \frac{2(|m_0| + |m_1|)\alpha}{v} \sin\left(\frac{v}{2(|m_0| + |m_1|)} k_{\delta f_{dc}}\right) \quad \text{(Eq. 9)}$$

Figure 9A:
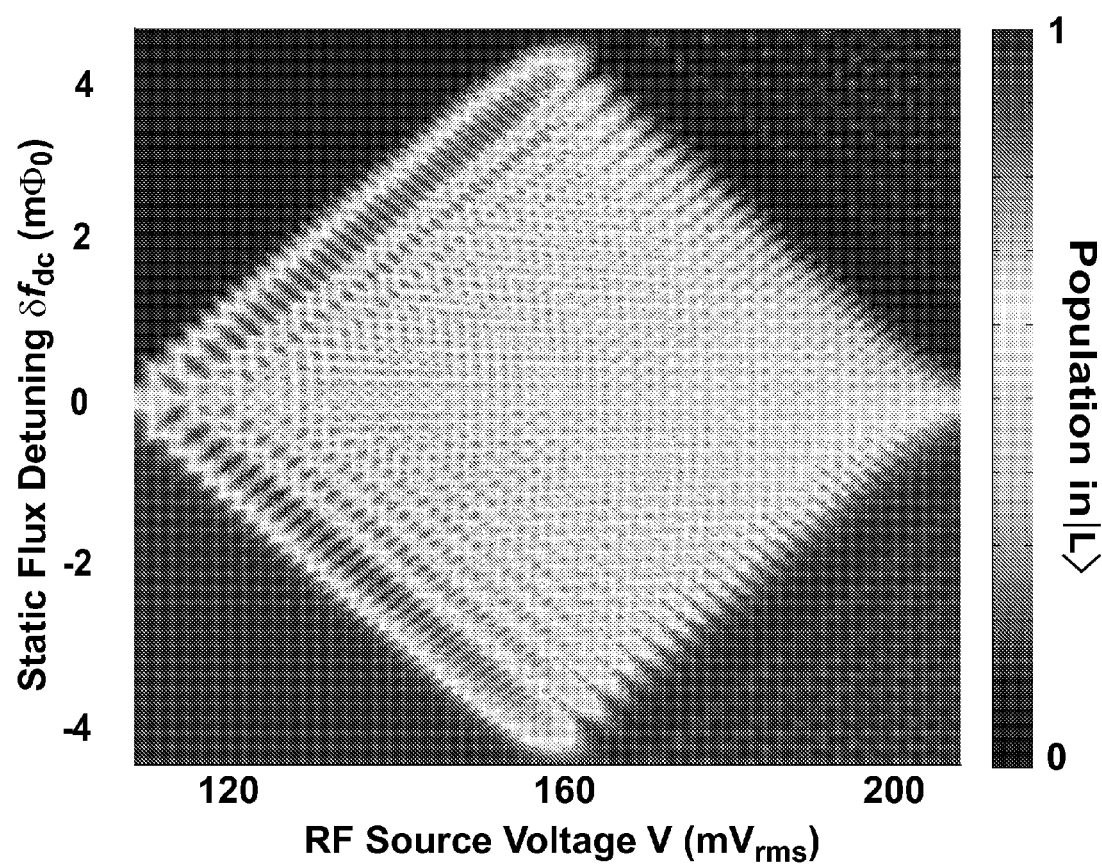
FIG. 9A is a close-up view of the second diamond of FIG. 6.
Figure 9B:
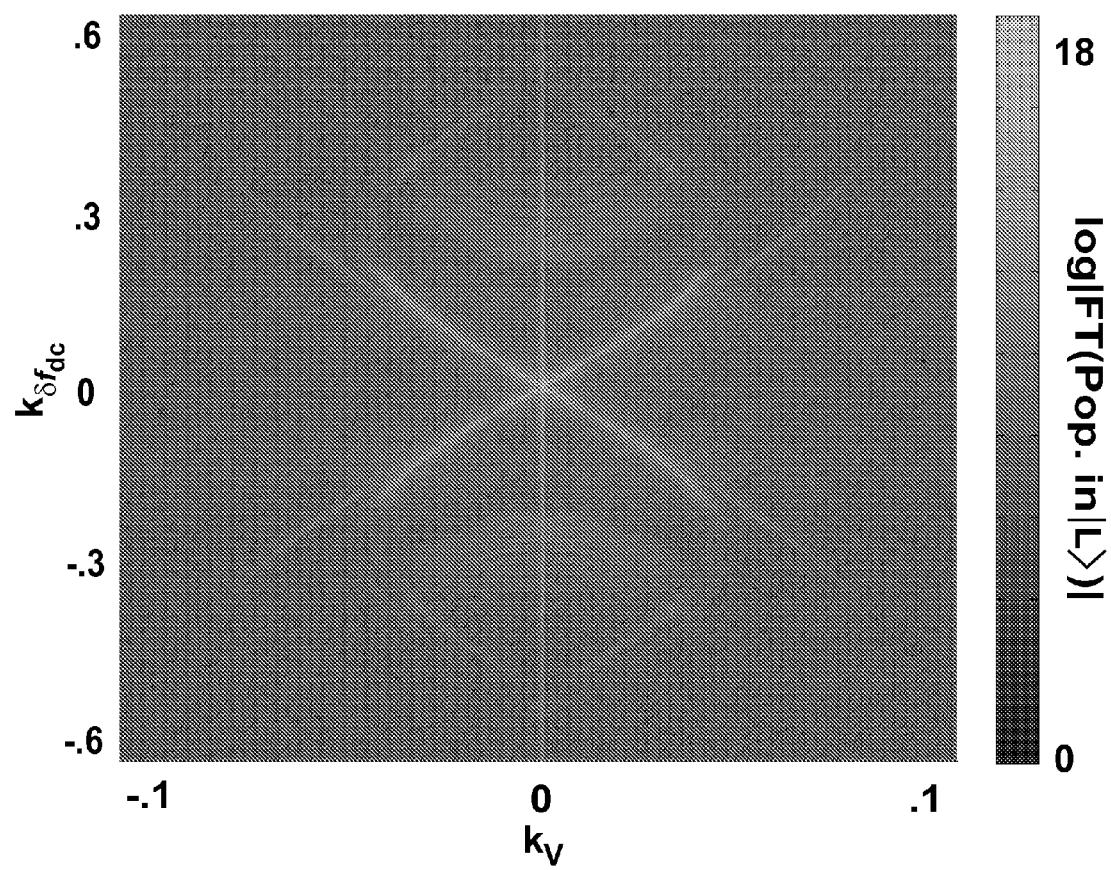
FIG. 9B is an illustration of the Fourier transform of the second diamond of FIG. 6.

The sinusoid has the period different from that of equation 7 by the ratio of the slopes $2|m_0|/(|m_0|+|m_1|)$. Both sinusoids can be clearly identified in the Fourier transform of the second diamond, shown in FIG. 9B, where FIG. 9A is a close-up view of the second diamond of FIG. 6, which indicates that all three transitions at the $\Delta_{0,0}$ crossing and the $\Delta_{0,1}$ ($\Delta_{1,0}$) crossings indeed contribute to the pattern observed in the second diamond (D2). From the measured ratio of the sinusoids' periods we obtain the ratio of the slopes of the qubit energy levels $m_0 = m_1$ without any fitting parameters.

Another important feature of 2DFT of the higher diamonds D2, D3 and D4, as compared to D1, is that only portions of the principal sinusoids (equation 5) are visible in Fourier images. This can be understood from the stationary phase analysis of the Fourier integrals, which yields a mapping between rays in "real space" (V, $\delta f_{dc}$) and points in Fourier space ($k_V, k_{\delta f_{dc}}$). This tomographic ray-to-point mapping originates from the fact that the pattern of Stückelberg interference fringes is characterized by position-dependent wave-vectors, which are constant along the rays as shown by equation 10 (Eq. 10).

$$\frac{\delta f_{dc}}{\alpha V} = u, \quad -1 < u < 1 \quad \text{(Eq. 10)}$$

In equation 10, u is the slope parameter used to label different rays. The rays of equation 10 are mapped to the points in Fourier space given by equation 11 below, $$(k_{\tilde{V}}, k_{\tilde{\delta f}_{dc}}) = \pm \frac{2}{v}(\pm\sqrt{1-u^2}, \arccos u + \pi n) \quad \text{(Eq. 11)}$$

$$= \pm \frac{2}{v}(\pm \sin\theta, \theta + \pi n)$$

where n=0, ±1, ±2 ..., θ=arcos u, and tilde denotes the quantities rescaled in the same way as in Eq. 5.

Taking the second diamond D2 as an example, it is noted that in its Fourier transform the real-space integration samples a more limited sector of the fringes arising from each of the avoided crossings as compared to the first diamond D1. The constraints on the rays of equation 10 can be approximately described as $$-\frac{1}{3} < u < \frac{1}{3}$$

for the fringes originating from the $\Delta_{0,0}$ crossing, and as $$\frac{1}{3} < u < 1 \text{ and } -1 < u - \frac{1}{3}$$

for the fringes originating from the $\Delta_{0,1}$ and $\Delta_{1,0}$ crossings. This means that there is a gap around the peak of the sinusoid of equation 9, for equation 12 below.

$$\frac{v}{2(|m_1|+|m_0|)} k_{\delta f_{dc}} \approx (n+1/2)\pi \quad \text{(Eq. 12)}$$

It is noted that in the sinusoid of equation 7, there is a gap around the nodes reflected by equation 13 below.

$$\frac{v}{4|m_0|} k_{\delta f_{dc}} \approx n\pi \quad \text{(Eq. 13)}$$

Using the formulas of equation 11, these restrictions can be more conveniently expressed as $-k_v^* < k_{\tilde{v}} < k_v^*$ for the sinusoids of equation 9, and $|k_{\tilde{v}}| > k_v^*$ for the sinusoid of equation 7, with equation 14 below determined from the limiting slope $u^* = \frac{1}{3}$ of the rays constrained by the size of the second diamond D2.

$$k_V^* = \frac{2}{v}\sqrt{1-\left(\frac{1}{3}\right)^2} = \frac{2}{v}\sqrt{8/9} \quad \text{(Eq. 14)}$$

It is noted that the actual size of the arcs visible in 2DFT of the second diamond D2 is slightly bigger than suggested by this estimate, because the Fourier integral samples all the points in the rectangle in FIG. 9A rather than just the points within the second diamond D2.

The restriction of the phase space sampled by 2DFT becomes even more stringent for higher diamonds D3 and D4, rendering the 2DFT approach as it was developed here less useful for extracting spectroscopic information from these diamonds. Instead, it is noted that in the third diamond D3 and the fourth diamond D4 it is more efficient to extract the desired information directly from the short-time dynamics.

Slope Extraction from Landau-Zener-Stückelberg Interference Patterns

The following technique provides an example of one way to determine the energy band slopes. The interference between sequential Landau-Zener transitions at an isolated avoided crossing is sensitive to the relative phase shown by equation 15 below accumulated by the two components of the wave function between the first and second traversals of the avoided crossing.

$$\Delta\phi = 2\pi \int_{t_1}^{t_2} \Delta E(t')\,dt' \quad \text{(Eq. 15)}$$

Here $\Delta E(t')$ is the instantaneous diabatic energy level separation at time $t'$, and $t_{1,2}$ are the times of the first and second traversals, respectively. We note that the energy $\Delta E$ is measured in frequency units (GHz), which is equivalent to setting $h=1$; this is why the expression contains the factor $2\pi$ rather than $1/\hbar$.

For demonstration, we focus on the interference in the first diamond D1 where the driving, as shown by equation 16, sweeps the qubit 30 through only the lowest avoided crossing $\Delta_{0,0}$.

$$\delta f(t) = -\delta f_{dc} + \alpha V \sin \omega t \quad \text{(Eq. 16)}$$

Using the definition of the energy level slopes given in the text, $m_q = dE_q/df$ in units of energy per flux, and approximating the driving $\delta f(t)$ near the maximum of $\sin \omega t$ by a parabola, we write the energy difference of the states $|0, L\rangle$ and $|0, R\rangle$ as shown by equation 17 below.

$$\Delta E(t) \approx 2|m_0|(\alpha V - \delta f_{dc}) - |m_0|\alpha V \omega^2 (t-T/4)^2 \quad \text{(Eq. 17)}$$

In equation 17, $T = 2\pi/\omega$ is the period of the driving signal, and $m_0$ is the energy-level slope of the ground state (assumed to be equal in magnitude for the left and right wells).

By setting $\Delta E(t^*) = 0$, it is noted that the initial and final crossing times $t_{1,2} = T/4 \mp t^*$, with $t_* = \sqrt{2(\alpha V - f_{dc})/\alpha V \omega^2}$. In the parabolic approximation to the driving signal, of equation 17, the phase accumulated between crossings is shown by equation 18.

$$\Delta\phi = 2\pi \int_{t_1}^{t_2} \Delta E(t)\,dt = 2|m_0|\frac{8\pi}{3}(\alpha V - \delta f_{dc})t_* \quad \text{(Eq. 18)}$$

Using the quantization condition for interference, $\Delta\phi = 2\pi N$, and the definition of $t^*$, we find the values of static flux detuning $\{\delta f_{dc}^{(N)}\}$, where constructive interference occurs, to be as shown by equation 19 below.

$$2\pi N = 2|m_0|\frac{8\pi\sqrt{2}}{3}\frac{(\alpha V - \delta f_{dc}^{(N)})^{3/2}}{(\alpha V)^{1/2}\omega} \quad \text{(Eq. 19)}$$

Rearranging equation 19 and using $\omega = 2\pi\nu$ we find the interference-node positions as shown by equation 20 below.

$$\delta f_{dc}^{(N)} = \alpha V - s_{0,0} N^{2/3}, \quad s_{0,0} = \left(\frac{3\pi\nu}{2\sqrt{2}}\frac{\sqrt{\alpha V}}{2|m_0|}\right)^{2/3} \quad \text{(Eq. 20)}$$

Equation 20 can be generalized to any avoided crossing $\Delta_{q,q'}$ by making the replacement $2|m_0| \to |m_q| + |m_{q'}|$, from which we arrive at equation 17. Since the value of a can be independently obtained from the shape of the observed amplitude-spectroscopy diamonds, the relations of equation 20 can be used to determined the energy band slopes $m_q$ from the data.

Fresnel-like Oscillations in the Landau-Zener Dynamics

Information may also be extracted from the application of amplitude spectroscopy over short time scales, in addition to saturated driving.

The time-dependent oscillations observed in temporal-response measurements result from Larmor precession about a tilted axis following the qubit's transit through an avoided crossing. In the regime where the Landau-Zener transition probability is small, we use a perturbative model to relate these oscillations to the well-known Fresnel integral.

By linearizing the sinusoidal driving signal $\delta f(t) = -\delta f_{dc} + \Phi_{rf} \sin \omega t$ near the moment of traversal through the avoided crossing, $t_* = \omega^{-1} \arcsin(\delta f_{dc}/\Phi_{rf})$, we arrive at the familiar Landau-Zener Hamiltonian shown by equation $$'H(t) = (\hbar/2)(\beta t \hat{\sigma}^z + \Delta \hat{\sigma}^x), \beta = A_{q,q'} \Phi_{rf} \omega \cos \omega t, \quad \text{(Eq. 21)}$$

where $\beta$ is the sweep velocity, the detuning $\delta f_{dc}$ is measured from the level crossing, $\Delta = \Delta_{q,q'}$ is the energy splitting, and $A_{q,q'} = h(|m_q| + |m_{q'}|)$ is the energy-flux conversion factor. Next, we transform to a non-uniformly rotating frame by $|\psi_R(t)\rangle = e^{i\Phi(t)\hat{\sigma}^z}|\psi(t)\rangle$ with $$\phi(t) = -\frac{1}{2\hbar}\int_0^t \beta t' \, dt' = -\frac{1}{4\hbar}\beta t^2.$$

The rotating frame Hamiltonian is purely off-diagonal as shown by equation 22 below.

$$'H_R = \frac{\hbar}{2}\begin{pmatrix} 0 & \Delta_R(t) \\ \Delta_R^*(t) & 0 \end{pmatrix}, \Delta_R(t) = \Delta e^{-i\beta t^2/2\hbar} \quad \text{Eq. (22)}$$

We the expand the system's time evolution operator $U(t, t_0)$ to first order in $\Delta$, providing equation 23 below.

$$U(t, t_0) = \hat{1} - \frac{i}{\hbar}\int_{t_0}^t {}'H_R(t') dt' + O(\Delta^2) \quad \text{Eq. (23)}$$

This approach is valid when the driving conditions are far from adiabatically. i.e., $\Delta^2/\beta'1$. The probability $P(t) = |\langle \uparrow | U(t,t_0) | \downarrow \rangle|^2$ to find the system in the state $|\downarrow\rangle$ at time t given that it started in the state $|\downarrow\rangle$ at $t0'$-$^t/\beta$ is given by equation 24 below.

$$P(t) = \frac{\Delta^2}{4}\left|\int_{t_0}^t e^{-i\beta t'^2/2\hbar} dt'\right|^2 \approx \frac{\Delta^2}{4}\left|\int_{-\infty}^t e^{i\beta t'^2/2\hbar} dt'\right|^2 \quad \text{Eq. (24)}$$

The oscillatory dependence of the integral of equation 24 on the final time t can be verified with the help of the Cornu spiral.

Detailed fitting of the observed oscillations for the states $|0,L\rangle$ and $|2,R\rangle$ requires simulating the full Bloch dynamics with the sinusoidal driving and smooth pulse turn-off after the RF pulse ends at $t = \Delta t$, as well as taking into account intrawell relaxation after the LZ transition. For that we use a non-Hermitian Hamiltonian, as shown by equation 25, below.

$$'H = \frac{\hbar}{2}\begin{pmatrix} \dot{o}(t) & \Delta_{q,q'} \\ \Delta_{q,q'} & -\dot{o}(t) - i\gamma \end{pmatrix}, \quad \text{Eq. (25)}$$

$$\hbar\dot{o}(t) = \begin{cases} A_{q,q'}\delta f(t), & t < \Delta t \\ A_{q,q'}(\delta f(t) - \Phi_{rf} g(t - \Delta t)^2), & t > \Delta t \end{cases}$$

In equation 25, q=0, q'=2, and $\delta f(t)$ is the driving signal given by equation 16.

For exemplary purposes, we estimate $\Delta_{0,2} = (2\pi)0.395$ GHz from the asymptotic Landau-Zener transition probability using the detuning-dependent value of $\beta$ quoted above in equation 21, with the slopes $m_q$, $m_{q'}$ obtained from the analysis of Stückelberg oscillations. With these values, we solve the Schrödinger equation $i\hbar d\psi/dt = 'H\psi$ with the Hamiltonian of equation 25 and from the best fit to the data determine the intrawell relaxation rate $\gamma = (2\pi)0.65$ GHz and the pulse turn-off parameter $g = 0.32$ ns$^{-2}$. The large value of the intrawell relaxation rate obtained from fitting the data indicates that $\gamma$ in the model of equation 25 accounts for the cumulative effect of several factors, such as phase jitter of the driving signal and decoherence of the qubit excited states, altogether overwhelming the effect of the intrawell relaxation. Based on a contrast reduction of the Stückelberg oscillations by approximately a factor 20 over 4 ns, we estimate a lower bound on the intrawell relaxation time to be 4 ns/ln(20)≈1.3 ns.

Gap and Slope Extraction from Amplitude Spectroscopy Over Short Time Scales

The temporal oscillations, or 'ringing', can be understood qualitatively in a pseudo-spin ½ A picture, in which the qubit states are identified with up-and down-spin states relative to a fictitious z axis. The qubit 30 undergoes Larmor-type precision about a tilted effective magnetic field, which steadily increases in magnitude and rotates towards the z axis as the qubit 30 leaves the avoided-crossing region. This picture is consistent with a temporal analysis of the canonical Landau-Zener problem, in which a linear ramp with velocity $\beta$ sweeps the qubit 30 through the avoided crossing. In the perturbative (non-adiabatic) limit, this model yields the transition probability shown in equation 26 below.

$$P(t) = \frac{\Delta_{0,2}^2}{4}\left|\int_{-\infty}^t e^{i\beta t'^2/2\hbar} dt'\right|^2 \quad \text{Eq. (26)}$$

The integral in equation 26 often arises in the context of optical diffraction.

To obtain a quantitative fit we account for decoherence and the non-abrupt ending of the pulse, which adds a small Stückelberg-type interference contribution. We find good agreement between the data and a simulation of the Bloch dynamics of the two-level system near $\Delta_{0,2}$, Which includes longitudinal sinusoidal driving up to time $t = \Delta t$ followed by a rapid turn-off transient over approximately, for example. 2 ns, and a decoherence rate of $2\pi \times 0.65$ ns$^{-1}$. This large value is dominated by intra-well relaxation and phase jitter. The value of $\Delta_{0,2}$ can be extracted as a fining parameter and, in this regime, is largely insensitive to the details of the pulse transient and decoherence. Although the resulting coherence times are relatively short in comparison with the driving period, they are comparable to the typical Larmor frequency, set by the sweep rate, which allows us to observe coherent oscillations. Furthermore, as the qubit 30 is swept back through the $\Delta_{0,2}$ crossing, the interference that occurs at the second Landau-Zener transition mediates the conversion of temporal Larmor-type oscillations into Stükelberg steady-state oscillations.

As in the case of the stationary driving, the energy-level slopes can be extracted from the Stückelberg fringes using the $N^{2/3}$ power-law fitting and equation 4 above. We infer $m_2$ and $m_3$ from the sums $m_0 + m_2 = 2.189$ GHz m$\Phi_0^{-1}$ and $m_0 + m_3 = 1.929$ GHz m$\Phi_0^{-1}$. We use the short-time amplitude spectroscopy procedure to obtain $\Delta_{q,q'}$ for diamond D2-D4 and slopes $m_q$ for diamonds D3 and D4, as summarized in table 1.

Returning to FIG. 4, the energy level structure derived from analysis of the amplitude spectroscopy response may then be used to uniquely identify the atom (block 208). Specifically, while in many cases it may be sufficient to derive the energy level structure of the atom, in other cases it may be beneficial to identify the atom. In the latter circumstance, the storage device 106 in the computer 100 may have energy level structures (including the energy gaps, their positions, and energy level slopes) of specific atoms stored therein and the computer 100 may search the same to identify the atom. In other cases, it may be sufficient to determine the presence or absence of such an atom, molecule, defect, or impurity. In the case of tunable atoms, molecules, defects, or impurities, the amplitude spectroscopy indicates how the energy levels change with respect to the external control field or tuning parameter, which itself may be used for classification.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A system for providing amplitude spectroscopy of a multilevel quantum system, comprising:
    a generator for providing a waveform for analysis of a multilevel quantum system, wherein the generator has the capability of changing amplitude of the waveform provided and driving the multilevel quantum system at a fixed frequency while sweeping amplitude;
    a detector for reading population in different energy states of the multilevel quantum system, wherein the detector plots an amplitude spectroscopy response of the multilevel quantum system;
    a memory; and
    a processor configured by the memory to perform the step of plotting an energy-level diagram of the multilevel quantum system from the amplitude spectroscopy plot of the multilevel quantum system.

2. The system of claim 1, wherein the multilevel quantum system is selected from the group consisting of atoms, molecules, defects, and impurities with multiple energy levels.

3. The system of claim 1, wherein the processor is further configured by the memory to perform the step of uniquely identifying the multilevel quantum system by use of the energy level structure derived from analysis of the amplitude spectroscopy response.

4. The system of claim 1, wherein the detector is a superconducting quantum interference device magnetometer.

5. The system of claim 1, wherein the processor is further configured by the memory to perform the step of analyzing the amplitude spectroscopy response and deriving energy level slopes of the multilevel quantum system.

6. The system of claim 1, wherein the processor is further configured by the memory to perform the step of analyzing the amplitude spectroscopy response and deriving values of avoided crossings.

7. The system of claim 1, wherein the processor is further configured by the memory to perform the step of analyzing the amplitude spectroscopy response and deriving positions of avoided crossings.

8. A system for providing amplitude spectroscopy of a multilevel quantum system, comprising:
    logic configured to drive the multilevel quantum system at a fixed frequency, while sweeping amplitude;
    logic configured to plot amplitude spectroscopy response of the multilevel quantum system driven toward saturation, where the amplitude spectroscopy response reflects a fixed frequency and a sweeping amplitude; and
    logic configured to analyze the amplitude spectroscopy response of the multilevel quantum system to derive an energy level structure of the multilevel quantum system.

9. The system of claim 8, wherein the multilevel quantum system is selected from the group consisting of atoms, molecules, defects, and impurities with multiple energy levels.

10. The system of claim 8, further comprising logic configured to uniquely identify the multilevel quantum system by use of the energy level structure derived from analyzing the amplitude spectroscopy response.

11. The system of claim 8, wherein the system further comprises logic configured to analyze the amplitude spectroscopy response and derive energy level slopes of the multilevel quantum system.

12. The system of claim 8, wherein the system further comprises logic configured to analyze the amplitude spectroscopy response and derive values of avoided crossings.

13. The system of claim 8, wherein the system further comprises logic configured to analyze the amplitude spectroscopy response and derive positions of avoided crossings.

14. A method of providing amplitude spectroscopy of a multilevel quantum system, comprising the steps of:
    driving the multilevel quantum system at a fixed frequency, while sweeping amplitude;
    determining an amplitude spectroscopy response of the multilevel quantum system, where the amplitude spectroscopy response reflects a fixed frequency and a sweeping amplitude; and
    analyzing the amplitude spectroscopy response of the multilevel quantum system to derive an energy level structure of the multilevel quantum system.

15. The method of claim 14, wherein the multilevel quantum system is selected from the group consisting of atoms, molecules, defects, and impurities with multiple energy levels.

16. The method of claim 14, further comprising the step of uniquely identifying the multilevel quantum system by use of the energy level structure derived from analyzing the amplitude spectroscopy response.

17. The method of claim 14, further comprising the step of analyzing the amplitude spectroscopy response to derive energy level slopes of the multilevel quantum system.

18. The method of claim 14, further comprising the step of analyzing the amplitude spectroscopy response to derive values of avoided crossings.

19. The method of claim 14, further comprising the step of analyzing the amplitude spectroscopy response to derive positions of avoided crossings.

20. The method of claim 14, wherein the step of driving the multilevel quantum system further comprises driving the multilevel quantum system over time scales such that the multilevel quantum system approaches saturation.

21. The method of claim 14, wherein the step of driving the multilevel quantum system further comprises driving the multilevel quantum system over time scales such that the multilevel quantum system exhibits a time dependent amplitude spectroscopy response.

* * * * *